US00PP08760P

United States Patent [19]

Schumann

[11] Patent Number: Plant 8,760

[45] Date of Patent: May 31, 1994

[54] GERANIUM PLANT NAMED FISGRAND

[75] Inventor: Ingeborg Schumann, Albstadt, Fed. Rep. of Germany

[73] Assignee: Florfis AG, Binningen, Switzerland

[21] Appl. No.: 94,683

[22] Filed: Jul. 21, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Foley & Lardner

[57] ABSTRACT

A new and distinct cultivar of geranium plant named Fisgrand, particularly characterized by the combined features of orange red flower color, semi-double flower form, medium green foliage with strong zonation, and medium to early flower response.

1 Drawing Sheet

1

The present invention comprises a new and distinct cultivar of geranium, botanically known as *Pelargonium zonale* l'Hert, and hereinafter referred to by the cultivar name Fisgrand.

Fisgrand is a product of planned breeding program which had the objective of creating new geranium cultivars with orange red flower color, semi-double flower form, medium green foliage with zonation, medium growth habit, all in combination with comparatively early spring flower response.

Fisgrand was originated from a hybridization made by the inventor Ingeborg Schumann in a controlled breeding program in Galdar, Gran Canaria, Spain in 1986. The female parent was a seedling identified by the number I 83/764/3, derived by selfing a seedling obtained by a cross between the unpatented cultivar Tetra Scharlach and a cultivar from a tetraploid line from the unpatented cultivar Stadt Bern. Tetra Scharlach is characterized by single scarlet red flowers and leaves without zonation. Stadt Bern has orange red flowers and dark green foliage with very strong zonation.

The male parent of Fisgrand was the patented variety Achspen, disclosed in U.S. Plant Pat. No. 5,313 under the varietal name Lachsball. Achspen is characterized by its compact habit, light salmon flowers and foliage without zonation.

Fisgrand was discovered and selected as one flowering plant within the progeny of the stated cross by Ingeborg Schumann in 1987 in a controlled environment in Galdar, Gran Canaria, Spain.

The first act of asexual reproduction of Fisgrand was accomplished when vegetative cuttings were taken from the initial selection in February 1988 in a controlled environment in Galdar, Gran Canaria by, or under the supervision of, Ingeborg Schumann.

Horticultural examination of plants grown from these outings initiated in May 1988, and continuing thereafter, has demonstrated that the combination of characteristics as herein disclosed for Fisgrand are firmly fixed and are retained through successive generations of asexual reproduction.

Fisgrand has not been observed under all possible environmental conditions. The phenotype may vary significantly with variations in environment such as temperature, light intensity and day length. The following observations, measurements, and comparisons describe plants grown in Hillscheid, Federal Republic of Germany under greenhouse conditions which approximate those generally used in commercial practice.

2

The following traits have been repeatedly observed and are determined to be basic characteristics of Fisgrand, which in combination distinguish this geranium as a new and distinct cultivar:

1. Orange red flower color
2. Large semi-double flowers
3. Medium green foliage
4. Strong zonation
5. Medium growth habit
6. Medium to early spring flower response Of the many commercial cultivars known to the present inventor, the most similar in comparison to Fisgrand is Isabell. Reference is made to attached Chart A which compares certain characteristics of Fisgrand to those same characteristics of Isabell. In general comparison to Isabell, Fisgrand has a more vigorous growth habit, stronger zonation, a little later flower response, and flowers which have better tolerance to heat.

The accompanying color photographic drawing shows typical flower and foliage characteristics of Fisgrand, with colors being as true as possible with illustrations of this type.

In the following description color references are made to The Royal Horticultural Society Colour Chart. The color values were determined indoors from plants grown indoors in June at Hillscheid, Federal Republic of Germany.

Classification:

*Botanical.*—A hybrid of the species *Pelargonium zonale* l'Hert.

*Commercial.*—Zonal geranium, cv. Fisgrand.

INFLORESCENCE

A. Umbel:

*Shape.*—Semi-spherical.

*Average diameter.*—105 mm.

*Average depth.*—65 mm.

*Peduncle length*—160 mm.

*Pedicel length.*—24 mm.

*Pedicel color.*—Main part dark red.

*Number of flowers per umbel.*—40–60.

B. Corolla:

*Average diameter.*—45 mm.

*Form.*—Semi-double.

*Number of petals.*—7–9.

*Number of petaloids.*—1–3.

*Color (general tonality from a distance of three meters).*—Orange red.

*Color of upper petals.*—40 A.
*Color of lower petals.*—40 A.
*Markings.*—No markings.
*Color of lower surface of petals.*—40 B.
*Number of sepals.*—5.
*Color of sepals.*—Green, with a spot of anthocyanine at the base.

C. Bud:
*Shape.*—Round to elliptic.
*Color (adaxial).*—Green, with a spot of anthocyanine at the base.
*Color (abaxial).*—Orange red.

D. Reproductive organs:
*Androecium.*—7–10 fertile anthers, white filament, yellow orange pollen.
*Gynoecium.*—5–6 lobed, red style and stigma.

E. Spring flowering response period: In Hillscheid, Federal Republic of Germany, in 1993 plants had on average 0.9 flowers opened 10 weeks after planting of unrooted cuttings.

F. Outdoor flower production: The flower count in 1992 in Hillscheid, Federal Republic of Germany indicated between 33 and 38 umbels per plant for May through August observation period.

G. Durability: Good shatter resistance.

PLANT

A. Foliage:
*Form.*—Kidney shaped, with open base.

*Margin.*—Bicrenated.
*Size of Leaf.*—10–11 cm.
*Color (upper surface).*—Medium green, approximately 137C.
*Color (zonation).*—Brown, approximately 166 A.
*Tolerance to botrytis.*—Average.

B. General appearance and form:
*Internode length.*—2–4 cm.
*Branching pattern.*—2.8 per plant, per week.
*Height (12 week old plant).*—7 cm.

CHART A

| Characteristic | FISGRAND | ISABELL |
|---|---|---|
| Color of lower surface of petal | orange red, uniform | orange red and white marbled |
| Zonation (1 weak-9 very strong | 7, strong | 5–7, medium-strong |
| Internodes | 2–4 cm | 1–2 cm |
| Plant height | 17 cm | 15 cm |
| Pedicel color | light red to dark red | green to light red |
| Beginning of flowering open flowers per plant (10 week old plants) | 0.9 | 1.1 |

It is claimed:

1. A new and distinct cultivar of geranium plant named Fisgrand, as illustrated and described.

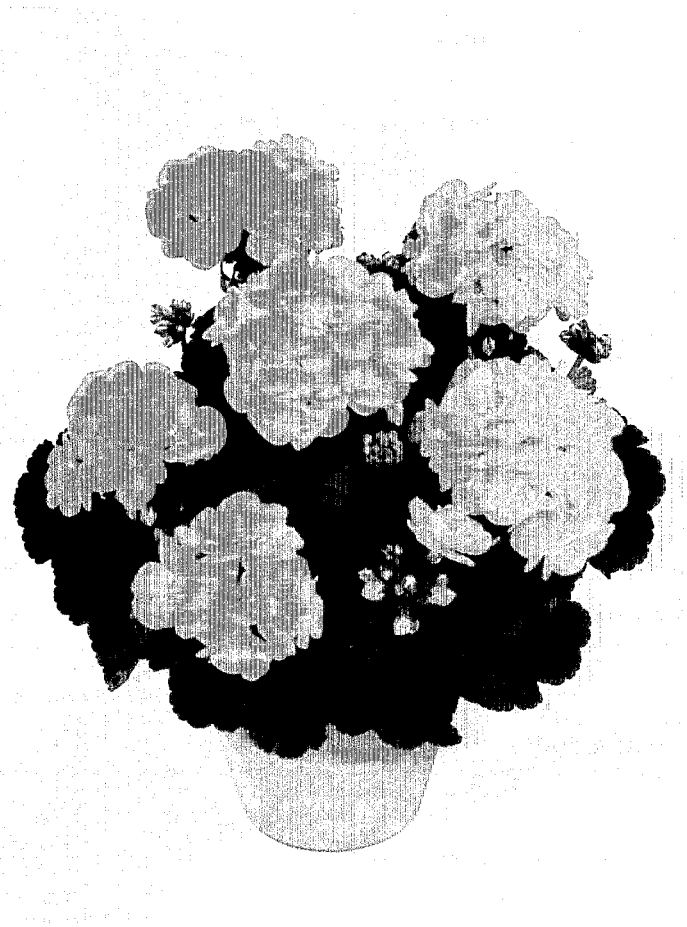

* * * * *